United States Patent [19]

Perdijon

[11] 4,173,899
[45] Nov. 13, 1979

[54] METHOD AND DEVICE FOR SCANNING BY MEANS OF A FOCUSED ULTRASONIC BEAM

[75] Inventor: Jean Perdijon, Saint Ismier, France

[73] Assignee: Commissariat a l'Energie Atomique, Paris, France

[21] Appl. No.: 905,518

[22] Filed: May 12, 1978

[30] Foreign Application Priority Data

May 16, 1977 [FR] France .................... 77 14886

[51] Int. Cl.² .......................................... G01N 29/04
[52] U.S. Cl. ........................................ 73/620; 73/633
[58] Field of Search ............... 73/620, 629, 633, 635, 73/640

[56] References Cited

U.S. PATENT DOCUMENTS

| | | | |
|---|---|---|---|
| 2,846,875 | 8/1958 | Grabendorfer | 73/620 |
| 3,575,042 | 4/1971 | Lovelace | 73/620 |
| 3,592,052 | 7/1971 | Giacomo et al. | 73/620 |
| 3,673,860 | 7/1972 | Flaherty et al. | 73/620 |

FOREIGN PATENT DOCUMENTS 1085624  2/1955  France ........................................ 73/633

Primary Examiner—Anthony V. Ciarlante

[57] ABSTRACT

A segment C′ located in a medium constituted by a test-piece is scanned by means of a focused ultrasonic beam formed by a focusing transducer which is immersed in a couplant fluid such as water. In order to displace a focal point of the ultrasonic beam within the test-piece and to scan the segment C′, the focus of the transducer is displaced in translational motion along a curve segment C which is the optical image of the segment C′ in the interface between the test-piece and the couplant fluid.

6 Claims, 3 Drawing Figures

METHOD AND DEVICE FOR SCANNING BY MEANS OF A FOCUSED ULTRASONIC BEAM

This invention relates to a method for scanning by means of a focused ultrasonic beam a segment C placed within a medium and especially a metallic medium such as the zone located in the vicinity of a welded joint, for example. The invention is also concerned with a device for carrying out said method.

If often proves necessary in accordance with known practice to carry out ultrasonic inspection of thick or massive parts at variable depth while maintaining the beam focused on the different points to be inspected.

In order to obtain good sensitivity, it is important to ensure maximum concentration of the ultrasonic waves in the vicinity of the point to be inspected. It is for this reason that the beams which emerge from the transducers are usually focused. Furthermore, it is usually desirable to maintain the incidence of the beam on the part at a constant value in order to generate waves of a well-defined type (longitudinal waves, transverse waves, Lamb waves and so forth) and to detect defects in well-determined orientation (the defects most clearly detected in echography are those which are perpendicular to the direction of the ultrasonic beam). The problem is therefore as follows: when it is desired to observe a segment in type B echography and then to sweep said segment in order to obtain a section of the material, then which is the best focusing transducer path out of the medium in which the welded joint is located? In the prior art, the transducers were usually displaced in a direction parallel to the interface between the part to be measured and the couplant medium in which the transducer is placed (such as water, for example). A displacement of this type is subject to a major disadvantage, however, by reason of the fact that, as will become apparent hereinafter, the sensitivity was not constant as a function of the displacement of the transducer and of the depth of the portion of the zone to be inspected.

As a general rule, the weld plane is at right angles to the interface between the medium containing the welded joint and the couplant medium in which the transducer is located. Full observation of the weld plane is carried out in two directions: a first displacement of the transducer parallel to the weld plane and parallel to the plane which separates the two media in order to sweep the weld plane in one direction; and a second displacement in a direction which is determined by the invention.

In the following description, it will be understood that the first medium designates the medium which is intended to provide coupling such as water, for example, and the second medium designates the part which is intended to undergo inspection.

It should first be recalled that a point F' of the second medium (part) would correspond to the point F of the first medium (water) if the refracting surface (between water and part) were to produce perfectly stigmatic correspondence. A segment C would in that case correspond to a segment C'. In order to ensure that the focus within the part describes the segment C', the focus F of the transducer need only describe the segment C in the absence of the part, thus producing a perfect image of the segment C' in the refracting surface. The path of the transducer can then be deduced from the path imposed on its focus.

Unfortunately, the correspondence is not stigmatic (except in the case of very small angles of incidence). The refracting surface causes two focal lines in the part (namely the sagittal and tangential focal lines, the circle of lower diffusion being located between the two) to correspond to the point focus F of a spherical focusing transducer in water (the focus being a virtual focus in the presence of the part). The procedure adopted then consists in sweeping the section plane P' to be studied with one of these focal lines (or with the circle of lower diffusion) and the plane P in which the virtual focus F of the transducer is intended to move is deduced therefrom by means of optical considerations.

The present invention permits sweeping of the section plane P' by means of a point focusing transducer obtained:
 either by giving a spherical shape to the piezoelectric pellet,
 or by placing a concave plane lens in front of a plane pellet.

In more precise terms, the invention is directed to a method for scanning with a focused ultrasonic beam a segment C' located in a second medium, the ultrasonic beam being formed by means of a focusing transducer placed within a first medium, said first and second media being separated by an interface. In order to displace a focusing point of the ultrasonic beam within the second medium and to scan said segment C', the invention essentially consists in producing translational displacement of the focus of the transducer along a curve segment C which is the optical image of the segment C' in said interface.

In a first preferential embodiment, the transducer is displaced in translational motion in such a manner that the tangential focal line of the ultrasonic beam emitted by said transducer in the second medium undergoes displacement along the curve segment C'.

In a second embodiment, the transducer is displaced in translational motion in such a manner that the sagittal focal line of the ultrasonic beam emitted by said transducer in the second medium undergoes displacement along the segment C'.

In a third embodiment, the transducer is displaced in translational motion in such a manner that the circle of lower diffusion of the ultrasonic beam emitted by said transducer in the second medium undergoes displacement along the segment C'.

As a general rule, the segment C can be assimilated with a straight line segment when C' is itself a straight line segment.

The combination of the two movements of the transducer in a direction parallel to the weld plane and in accordance with the movement contemplated by the invention makes it possible to scan a surface such as a weld zone, for example. Further distinctive features and advantages of the invention will become more readily apparent from the following description of exemplified embodiments which are given by way of explanation and not in any limiting sense, reference being made to the accompanying drawings, wherein.

Figure 1:
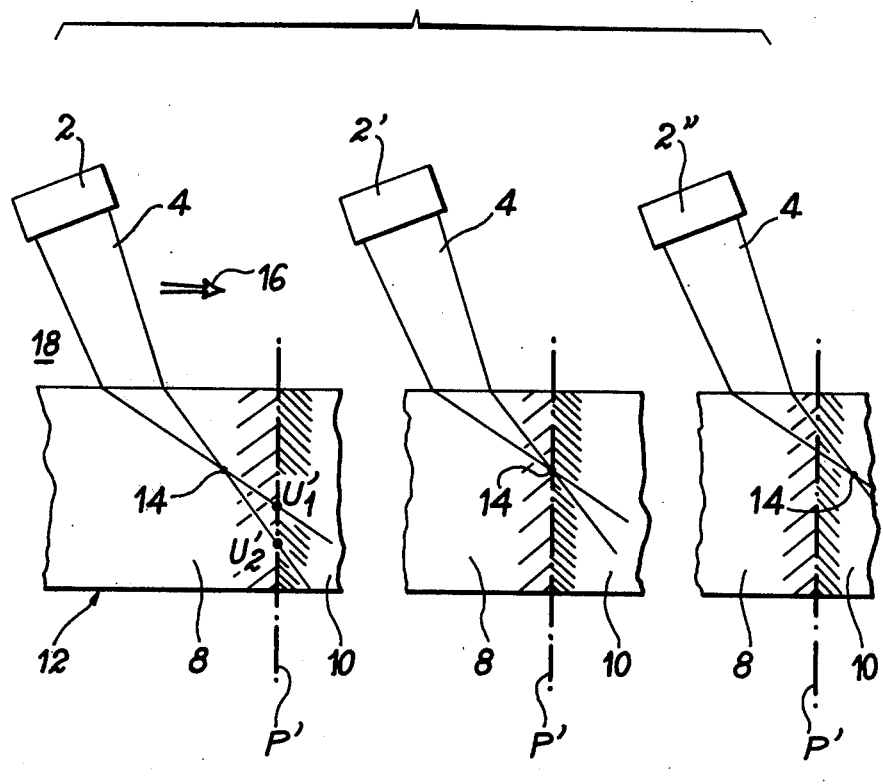
FIG. 1 is a diagrammatic illustration of focusing zone variations in the case of transducer displacements employed in the prior art.

In FIG. 1, there have been shown three successive positions 2, 2' and 2" of the transducer. These positions correspond to the usual displacement in accordance with conventional methods in which the transducer is displaced in translational motion parallel to the surface which lies between the coupling medium 18 and the medium 8 in which it is desired to inspect a weld zone containing the plane P'. The transducer 2 emits an ultrasonic beam 4 which is focused in the medium 8 containing the welded joint in the vicinity of the focal point 14. In position 2 of the transducer, the zone of the weld plane P' of the part 12 under observation, namely the plane which lies between the zones 8 and 10 of said part, is the segment $U_1' U_2'$. At the time of displacement of the transducer 2 in the direction of the arrow 16, a focused beam is directed onto the plane P' by the same transducer 2' since the focal point 14 coincides with the plane P' in this configuration. In position 2", the plane P' intersects the ultrasonic beam 4 before this latter reaches the focal point 14. As a result of this type of displacement, the concentration of ultrasonic waves in the different zones of the plane P' to be examined varies as a function of the depth. This proves unsatisfactory, however, since the sensitivity of detection of defects varies in the same proportion.

Figure 2:
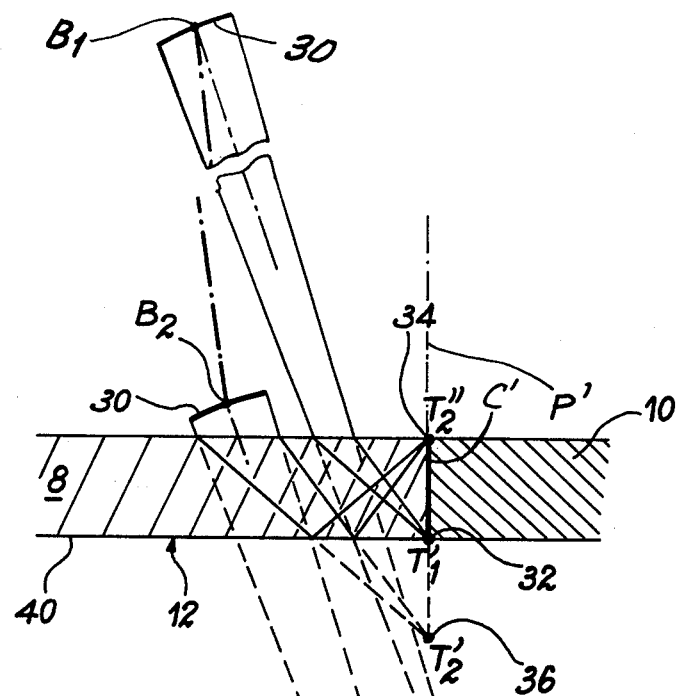
FIG. 2 shows the displacement carried out by a transducer in accordance with the invention in order to inspect a welded joint in the case in which said joint is located at right angles to the plane of the interface between the medium containing the welded joint and the coupling medium in which the transducer is located.
Figure 2:

FIG. 2 shows in greater detail the movement carried out by the emitting face 30 of the transducer in order to ensure that the energy which is focused along the tengential focal line in the medium 8 constituting the part 12 moves along the weld plane P'. In the particular case shown in this figure, the operation makes use of reflection from the bottom of the part. Thus in order to ensure that the tangential focal line undergoes displacement within the part on the segment C' from $T_1'$ to $T_2''$, said focal line should undergo displacement without reflection between $T_1'$ and $T_2'$. In position $B_1$ of the emitting face, the ultrasonic rays are focused on the bottom portion of the weld at the point 32 whereas, in position $B_2$, the ultrasonic rays are focused on the top portion 34 after reflection from the bottom interface 40 of the part 12. In any intermediate position, the beams are focused at any intermediate point of the weld zone P'. The operation is carried out with reflection in this case in order to prevent the point of incidence of the ultrasonic beam from being located in a zone which is too close to the plane P' since this zone is deformed by the weld and does not represent a suitable interface in which the angles of refraction are wholly constant.

The position of the focal point in the water is designated by the references $T_1$ and $T_2$ in respect of the two positions $B_1$ and $B_2$ of the transducer. Thus $T_1$ is the position of the focal point corresponding to a tangential image focal line at 32 in the part 12 and $T_2$ is the focal point corresponding to a tangential image focal line 36, namely the image of the point 34 in the plane mirror 40. The transducer is thus displaced along the segment $B_1-B_2$ which is parallel and equal to the segment C, from $T_1$ to $T_2$ in the method in accordance with the invention in order to inspect the weld with concentrations of constant energy. Thus in one example of construction, it has been found possible to inspect welded joints between metallic plates having a thickness of 20 mm; the plane of incidence was perpendicular to the plane P' and the excited waves were transverse waves which propagate through the steel part 12 at an angle of refraction of 45°. The angle of incidence in the water is of the order of 20.5°. As mentioned earlier, reflection from the inner face of the part 12 is utilized in order to avoid being hindered by irregularity of the refracting surface located between the part and the coupling medium in the vicinity of the weld fillet. In this case, in order to carry out complete scanning of the weld plane P' with the tangential focal line of a focused point transducer, the segment $T_1-T_2$ has a length of 93 mm and is inclined with respect to the normal at an angle of 9°.

Should it be found preferable to describe the weld plane with the sagittal focal line, the segment $B_1-B_2$ would be normal to the interface since it is readily apparent that the weld plane is at right angles to the surface of the part. Had it been decided to choose the circle of lower diffusion in the same example of FIG. 2, the segment $B_1-B_2$ would in that case be inclined at an angle of approximately 4.5°.

Figure 3:
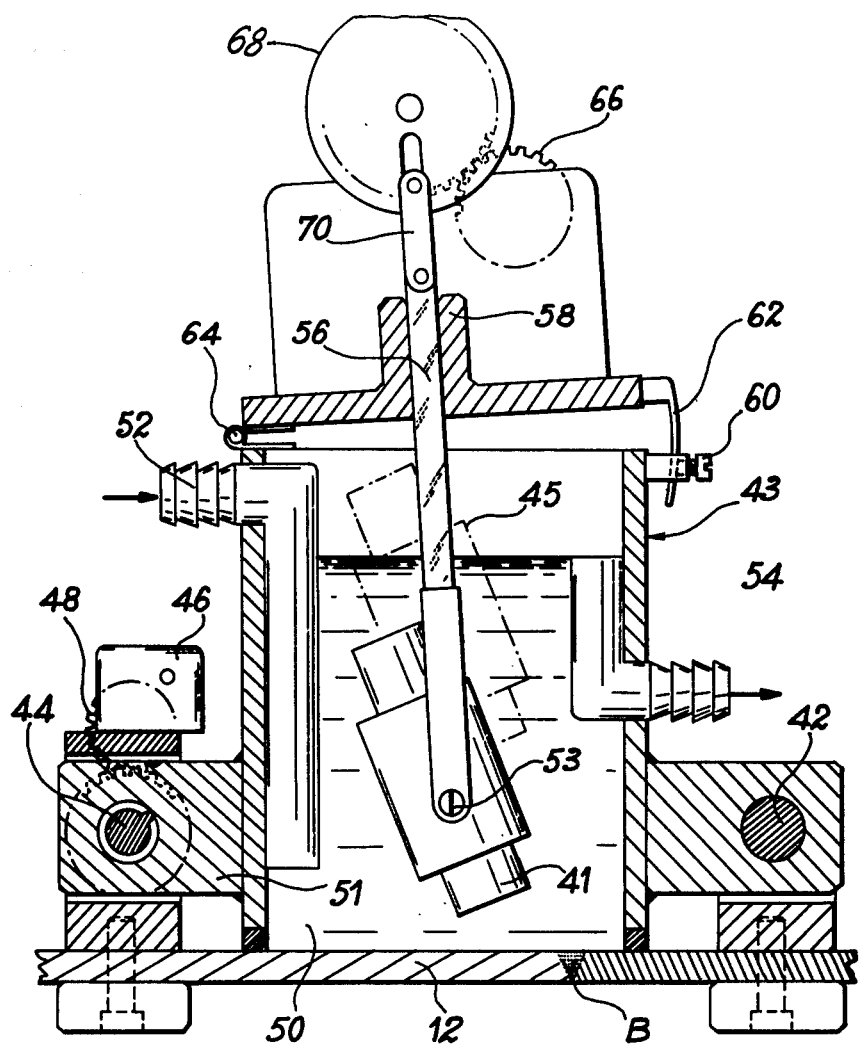
FIG. 3 is a constructional diagram of a device for displacing the transducer in accordance with the invention.

There is shown in FIG. 3 a device for carrying out a movement of displacement of the transducer as mentioned above. The bottom position of the transducer is shown at 41 and the top position is shown in chain-dotted lines at 45. The transducer can be moved in a direction at right angles to the figure by displacing the frame 43 which supports the transducer in sliding motion along guide cylinders 42 and 44. The frame 43 is driven along said cylinders by the driving unit 46 associated with the screw system 48. The weld fillet is shown at B in the part 12. The transducer is immersed in the coupling medium 50, namely the water which is supplied through the pipe 52 and discharged through the pipe 54. Leak-tightness is ensured by means of a sliding seal.

The angle of incidence of the ultrasonic beam on the part 12 is determined by the angle of inclination of the transducer 41 with respect to the vertical. This angle of inclination is fixed by tightening the screw 53 hard-up. The movement of the arm 56 which supports the transducer is fixed in an angular position by means of the guide sleeve 58, the angular position of said sleeve being determined by means of the clamping action produced by the screw 60 on the arm 62 which is rotatably mounted on the pin 64. Downward displacement of the transducer between the positions shown at 41 and 45 is obtained by means of a motor (not shown in the drawings). The wheel 66 driven by said motor is in turn intended to drive the wheel 68, the rigid arm 56 which carries the transducer being fixed on said wheel 68 by means of the link-arm 70. The amplitude of motion between the positions 41 and 45 is determined by the point of attachment of the link-arm 70 to the wheel 68.

What we claim is:

1. A method for scanning a segment C' located in a second medium by means of a focused ultrasonic beam formed by a focusing transducer placed in a first medium, said first and second media being separated by an interface, wherein a focal point of the ultrasonic beam is displaced in order to scan the segment C' aforesaid by displacing the focus of the transducer along a segment C which is the optical image of the segment C' in said interface.

2. A method according to claim 1, wherein the transducer is displaced in translational motion in such a manner that the tangential focal line of the ultrasonic beam emitted by said transducer in the second medium undergoes displacement along the segment C'.

3. A method according to claim 1, wherein the transducer is displaced in translational motion in such a manner that the sagittal focal line of the ultrasonic beam emitted by said transducer in the second medium undergoes displacement along the segment C'.

4. A method according to claim 1, wherein the transducer is displaced in translational motion in such a manner that the circle of lower diffusion of the ultrasonic beam emitted by said transducer in the second medium undergoes displacement along the segment C'.

5. A device for scanning a segment C' located in a second medium by means of a focused ultrasonic beam formed by a focusing transducer placed in a first medium, said first and second media being separated by an interface, wherein said device comprises mechanical means for displacing the focus of the transducer in translational motion along a segment C in such a manner that the segment C' is either all or part of the image of the segment C in the interface.

6. A device according to claim 5, wherein the segments C and C' are straight line segments and wherein the mechanical means carry out displacement of the transducer along a segment in a direction parallel to itself.

* * * * *